United States Patent
Vandali et al.

(10) Patent No.: US 7,561,709 B2
(45) Date of Patent: Jul. 14, 2009

(54) MODULATION DEPTH ENHANCEMENT FOR TONE PERCEPTION

(75) Inventors: Andrew Vandali, Greenvale (AU); Richard Van Hoesel, Reservoir (AU)

(73) Assignee: Hearworks PTY Limited, East Melbourne, Victoria (AU)

( * ) Notice: Subject to any disclaimer, the term of this patent is extended or adjusted under 35 U.S.C. 154(b) by 825 days.

(21) Appl. No.: 11/025,930

(22) Filed: Jan. 3, 2005

(65) Prior Publication Data

US 2005/0197832 A1 Sep. 8, 2005

Related U.S. Application Data

(60) Provisional application No. 60/613,230, filed on Sep. 28, 2004.

(30) Foreign Application Priority Data

Dec. 31, 2003 (AU) ............................... 2003907206

(51) Int. Cl.
  $H04R\ 25/00$ (2006.01)
(52) U.S. Cl. ................ 381/320; 381/312; 381/321
(58) Field of Classification Search ................ 381/104, 381/105, 106, 107, 312, 314, 320, 321, 323; 704/206, 226, 233; 700/94
See application file for complete search history.

(56) References Cited

U.S. PATENT DOCUMENTS

| 5,848,171 | A * | 12/1998 | Stockham et al. ............ 381/321 |
| 6,885,752 | B1 * | 4/2005 | Chabries et al. ............. 381/321 |
| 7,139,403 | B2 * | 11/2006 | Richardson et al. ......... 381/107 |

* cited by examiner

*Primary Examiner*—Huyen D Le
(74) *Attorney, Agent, or Firm*—Connolly Bove Lodge & Hutz LLP (57) ABSTRACT

A sound processing process is disclosed, with particular application to auditory prostheses. After input sound signals are processed into channels, an algorithm is applied to selectively increase the modulation depth of the envelope signals.

11 Claims, 8 Drawing Sheets

MODULATION DEPTH ENHANCEMENT FOR TONE PERCEPTION

CROSS-REFERENCE TO RELATED APPLICATIONS

This application makes reference to the following co-pending U.S. Patent Applications:

This application claims the priority of U.S. Provisional Patent Application No. 60/613,230, entitled, "Phase Alignment for Vocoder Based Speech Systems," filed on Sep. 28, 2004. The entire disclosure and contents of the above applications are hereby incorporated by reference.

The application is entitled "Phase Alignment for Voucher Based Speech Systems" filed concurrently, which claims priority from Australian Provisional Application No. 2003907206 filed Dec. 31, 2003. The entire disclosure and contents of the above patents and applications are hereby incorporated by reference.

BACKGROUND

Field of the Invention

This invention relates to the processing of signals derived from sound stimuli, particularly for the generation of stimuli in auditory prostheses, such as cochlear implants and hearing aids, and in other systems requiring sound processing or encoding. It further relates to software products and devices implementing such methods.

Voice pitch information can play an important role in speech perception as it provides cues to linguistic features such as intonation (question —statement contrast) and word emphasis (Highnam, & Morris 1987; Nooteboom, 1997; Wells, Peppe, & Vance, 1995), and also to paralinguistic features such as speaker identification and the emotional state of the speaker (Abberton & Fourcin, 1978; Liberman, & Michaels, 1962) and segregation of concurrent speakers (Brokx, & Nooteboom, 1982). Most importantly, voice pitch information is crucial for perception of tonal languages, such as Mandarin and Cantonese, where a change in fundamental voicing frequency within the same phonemic segment causes a change in lexical meaning (Lee et. al., 2002; Ciocca et. al., 2002). Pitch information is also of important to the appreciation of music where the frequency of the fundamental and its harmonics governs the pitch of the signal (Moore 1995).

Various speech processing strategies have been developed for processing of sound signals for use in stimulating auditory prostheses, such as cochlear prostheses and hearing aids. The multi-peak strategy (Seligman, Dowell, & Blamey, 1992; Skinner et. al., 1991) focused particularly on coding of aspects of speech, such as formants and the fundamental voicing frequency. For this strategy voice pitch information was predominantly coded by way of the electrical stimulation rate. Other strategies relied more on general channelization of the sound signal, such as the Spectral Maxima Sound Processor (SMSP) strategy, which is described in greater detail in Australian Patent No. 657959 and U.S. Pat. No. 5,597,390 by the present applicant. For this strategy voice pitch information (for a voicing frequency below approximately 200 Hz) is generally coded in the envelope signals of each channel by amplitude modulation at a frequency equal to or related to the voicing frequency.

Experiments conducted with users of cochlear implant prostheses have indicated that the frequency of amplitude modulated electrical signals can be reliably detected when the modulation depth is sufficiently deep (McKay, McDermott, & Clark, 1994).

Channelization of the sound signal, as is done by most speech coding strategies today, often results in modulation depths within individual channels of less than 6 dB, even though the broadband sound signal has voicing frequency modulation of greater than 6 dB.

It is an object of the present invention to provide a sound processing strategy, and associated devices and software, to improve the user's perception of voice pitch and musical tone.

SUMMARY

In a broad form, the present invention provides a sound processing strategy, of the type in which the sound signal is processed within defined frequency channels, wherein for at least some channels, when the modulation depth is less than a predetermined value, the modulation depth is increased.

Throughout the specification and claims, the term modulation depth in a channel means the ratio of the peak level to the trough level of the envelope signal in that channel over some finite time period.

According to one aspect, the present invention provides a sound processing process including at least the steps of:
(a) receiving a sound signal;
(b) processing said signal so as to produce a set of signals in spaced frequency channels; and
(c) performing further processing upon at least some of the set of signals;
wherein said process further includes the step of selectively increasing the modulation depth of the envelope signal for at least selected channels in response to a predetermined instruction set, prior to step (c).

From the prior studies of pitch perception, it appeared to the inventors that current channelization based speech processing strategies may not provide adequate coding for identification of modulation frequency in the channel envelop signals. It was thus hypothesised that expansion of the envelope signal modulation depth in cases when it was shallow may provide improved identification of the modulation frequency and thus the voicing or musical pitch of the sound signal. The present invention is applicable to processing sound signals for auditory prostheses, including cochlear implants and hearing aids, as well as other applications where it may be desirable to improve the perception of voice pitch or musical tone.

If desired in particular applications, only some channels could be processed as defined above, although this is not presently preferred.

The modulation depth may be expanded by some constant function when it is below a given threshold, in a smoothly varying fashion, or by different functions at defined breakpoints. Alternative parameters could be adjusted, which have the effect of expanding the modulation depth.

BRIEF DESCRIPTION OF THE DRAWINGS

An illustrative embodiment of the present invention will now be described with reference to the accompanying drawings, in which.

DETAILED DESCRIPTION

It will be appreciated that the present invention relates to an improvement which is applicable to a wide range of sound processing strategies for auditory prostheses, as well as other applications. Accordingly, the following implementation is not to be taken as limitative of the scope or applicability of the present invention.

An implementation will be described with reference to a cochlear implant sound processing system. The precise system employed is not critical to the applicability of the present system. The present implementation will be described with reference to its use with the SMSP strategy (McDermott, & Vandali, 1991; McDermott, McKay, & Vandali, 1992), which is similar to the SPEAK strategy (Skinner et. al., 1994; Whitford et. al., 1995) and Advanced Combinational Encoder (ACE) strategy (Vandali et. al., 2000). Note, however that it could equally be applied to other speech coding strategies such as the Continuous Interleaved Sampling (CIS) strategy (Wilson et. al., 1991).

Figure 1:
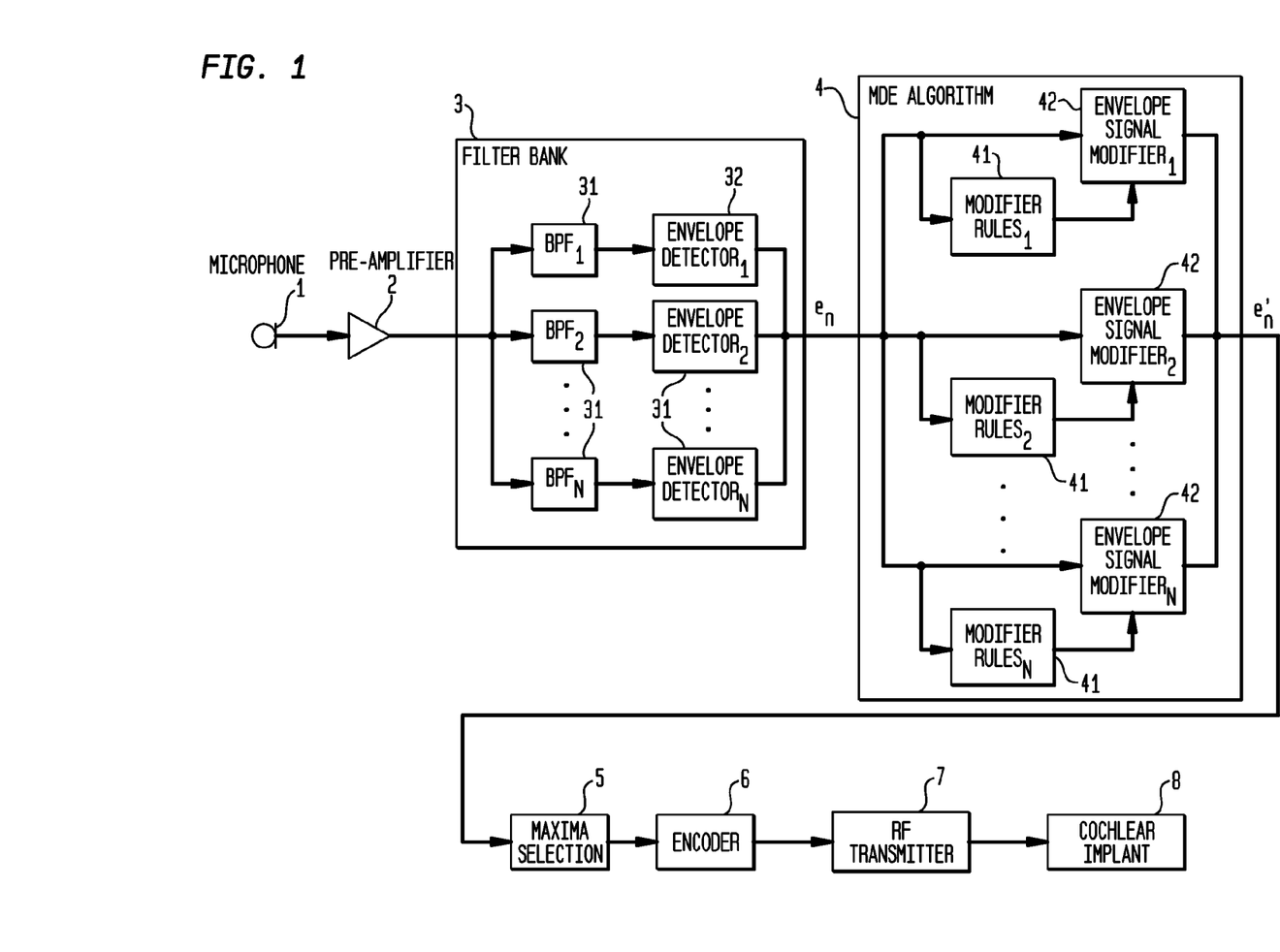
FIGS. 1 and 2 are schematic representation of the signal processing applied to the sound signal in accordance with the present implementation.
Figure 2:
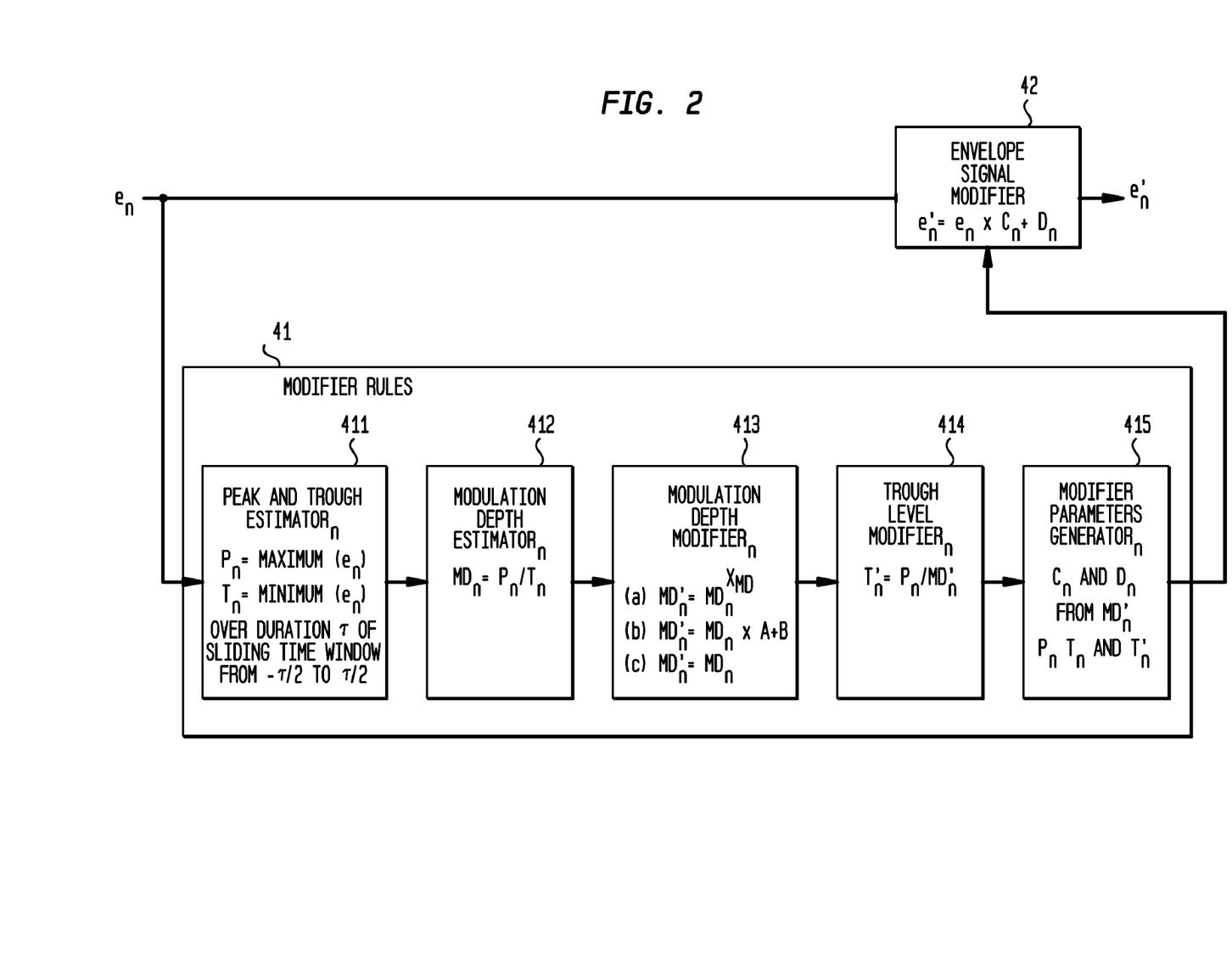

Referring to FIGS. 1 and 2, as with the SMSP strategy, electrical signals corresponding to sound signals received via a microphone 1 and pre-amplifier 2 are processed by a bank of N parallel filters 3 tuned to adjacent frequencies (typically N=16 for the conventional SMSP but in this implementation N can be varied and typically =20). Each filter channel includes a band-pass filter 31 and an envelope detector 32 to provide an estimate of the narrow-band envelope signal in each channel. The band-pass filters are typically narrow (approximately 180 Hz) for apical (low-frequency) channels and increase in bandwidth (typically up to 1000 Hz or more) for more basal (higher frequency) channels. The envelope detectors, which effectively comprise a full-wave (quadrature) rectifier followed by a low-pass filter, typically pass fundamental (modulation) frequency information up to approximately 180 Hz to 400 Hz but for some implementations higher frequencies can be passed.

In this embodiment either a Fast Fourier Transform (FFT) or a Finite Impulse Response (FIR) filter bank (which uses complex coefficients) could be employed to implement the filter bank. Both implementations effectively perform the band-pass filtering, full-wave (quadrature) rectification and low-pass filtering. The FFT filter bank provides a fixed low-pass filter cut-off frequency (for −3 dB gain) of 180 Hz. The complex coefficient FIR provides a low-pass filter cut-off frequency equal to the (−3 dB) bandwidth of the band-pass filters. Basal (high frequency) channels can be as wide as 1000 Hz or more and thus an additional $2^{nd}$ order low-pass filter (with a cut-off frequency of 400 Hz) can optionally be employed to remove any fine structure above the fundamental voicing frequency from the envelope signals. The advantage of employing the complex coefficient FIR over the FFT filter bank method is that higher voicing frequencies can be passed, provided that the band-pass filters are wider than 180 Hz.

The filter bank is used to provide an estimate of the envelope signals in each channel at regular time intervals known as the analysis or update rate. The SMSP strategy conventionally employs a relatively low analysis rate of approximately 250 Hz, however in this implementation a much higher update rate of approximately 1200 to 1600 Hz is employed so that modulation frequencies of approximately 300 to 400 Hz can be adequately sampled. Such update rates are available with current commercial cochlear implant systems and speech coding strategies such as ACE. It is known from amplitude modulation identification experiments with users of cochlear implant prostheses that update/stimulation rates of at least four times the modulation frequency are required for adequate analysis/coding of the signal (McKay, McDermott, & Clark, 1994).

The outputs of the N-channel filter bank are modified by the Modulation Depth Enhancement (MDE) algorithm 4, as described below, prior to further processing by the speech coding strategy. The MDE algorithm operates on the narrow-band envelope signals in each filter bank channel independently. The envelope signals in each channel are analysed so as to estimate the modulation depth 412 (i.e. the ratio of peak-to-trough amplitude 411) over some finite time period (τ).

The estimated modulation depth in each channel (MDn), where n refers to the channel number, is defined as shown in Eq. 1 below.

$$MDn=Pn/Tn \qquad (1)$$

where Pn=maximum (Peak) level and Tn=minimum (Trough) level of the envelope signal in each channel over some finite time period and are determined using a sliding time window of duration (τ).

The duration of the sliding time window (τ) is typically 10 to 15 ms and is sufficiently long enough to analyse fundamental voicing frequencies as low as 100 Hz. For periodic voiced signals such as vowels, the maximum and minimum levels will respectively follow peak and trough envelope signal levels relatively accurately provided that: the voicing period is shorter than the duration (τ) of the sliding time window; and that modulations in the signal at higher harmonic frequencies than the fundamental do not interfere with the modulation depth of the fundamental. For un-voiced signals, such as friction, which have no specific periodicity, the peak and trough levels (and thus the estimated modulation depth) can vary greatly from one peak-trough cycle to the next.

Because the modulation depth is estimated over some finite duration, rather than instantaneously, the estimate must be referenced from a time point corresponding to the middle of the time window. Thus a processing delay of τ/2 is introduced for all processing following the modulation depth estimation.

The estimated modulation depth (and hence the envelope signal) for each channel is modified 42, according to some rules (or input/output function) 41, so as to effectively increase the modulation depth in cases when it is small (shallow).

It will be appreciated that many alternatives exist for expanding the modulation depth, and that the example in this implementation is only one alternative. Various alternative implementations of the MDE algorithm are provided in Appendix A. The algorithm described in the first approach from Appendix A—Approach 1.A is summarised below.

In this implementation, a power function is used to expand the modulation depth for cases when it is less than some knee point (typically 6 dB). The order of the power function is typically 2 or 3. For modulation depths greater than this knee point but less than some limit (typically 20 dB), a linear function is used to modify the modulation depth. For modulation depths above this limit point the modulation depth is unchanged.

One possible set of rules for modification of the modulation depth 413 are defined as follows:

(a) For modulation depths less than or equal to some Knee point ($K_{MD}$), which typically equals 2 (6 dB), the modified modulation depth ($MD'_n$) is increased using a power function where the Expansion Factor ($X_{MD}$), which is typically equal to 2 or 3, defines the order of the power function.

$$MD'_n = MD_n^{X_{MD}} \text{ for } MD_n \leq K_{MD} \quad (2)$$

(b) For modulation depths greater than the Knee point but less than some Limit point ($L_{MD}$), which typically equals 10 (20 dB), the modulation depth is still increased but a linear function is employed. The constants A and B are calculated such that boundary conditions are satisfied (i.e. no discontinuities) at the knee and limit points.

$$MD'_n = MD_n \times A + B \quad (3)$$

for $K_{MD} < MD_n < L_{MD}$ and $K_{MD}^{X_{MD}} < L_{MD}$ where $A = (L_{MD} - K_{MD}^{X_{MD}})/(L_{MD} - K_{MD})$ and $B = L_{MD} \times (1-A)$ (c) For modulation depths above the Limit point the modulation depth is left unchanged.

$$MD'_n = MD_n \text{ for } MD_n \geq L_{MD} \quad (4)$$

Figure 3:
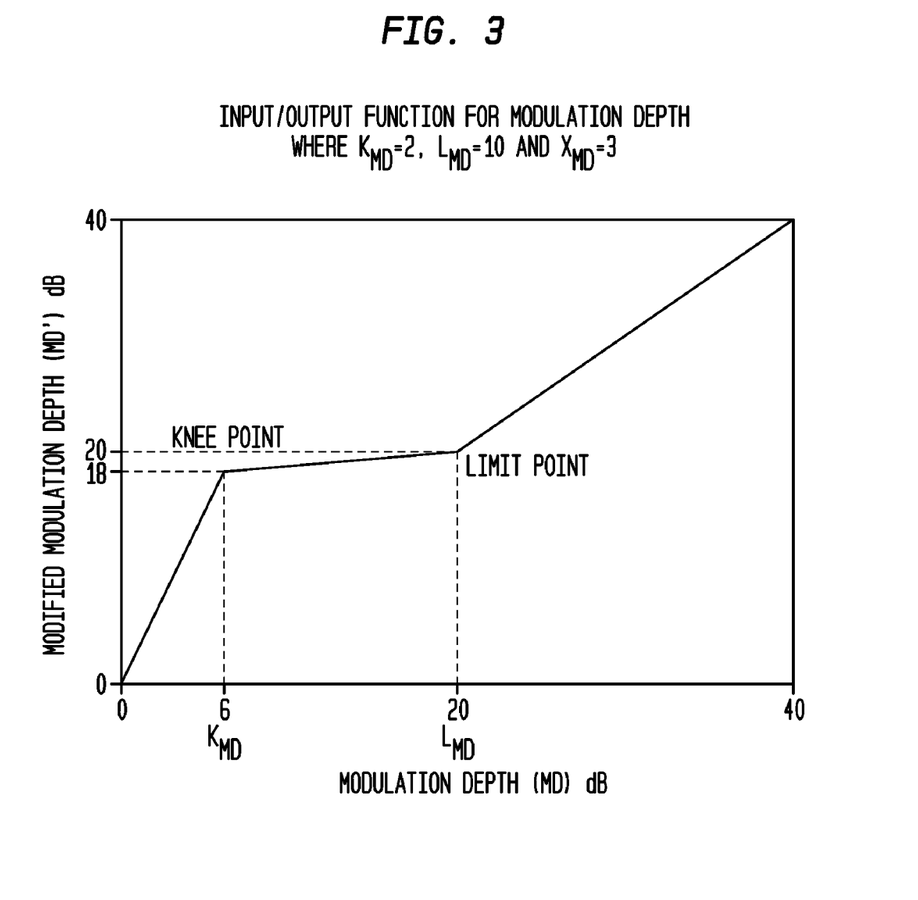
FIG. 3 depicts a typical input/output curve for the modulation depth.

FIG. 3 depicts an input/output curve, plotted on a log-log dB scale, for the modulation depth using a Knee point of 2 (6 dB) a Limit point of 10 (20 dB) and an Expansion factor of 3.

The modified modulation depth $MD'_n$ is used to adjust the trough $T'_n$ 414 level of the envelope signal such that the modified trough level $T'_n$ is reduced by the ratio of the original modulation depth over the modified modulation depth.

$$T'_n = T_n \times MD_n / MD'_n = P_n / MD'_n \quad (5)$$

However for points in time where the envelope signal is not at a trough, the envelope signal must be modified (e'n) based on the required reduction to the trough level. A linear equation (Eq. 6) can be employed to modify the continuum of levels in the envelope signal 42. The use of a linear function preserves the shape of the envelope signal within each voicing period (or periodic cycle).

$$e'_n = e_n \times C_n + D_n \quad (6)$$

where $C_n = (P_n - T'_n)/(P_n - T_n)$ and $D_n = P_n \times (1 - C_n)$

Figure 8:
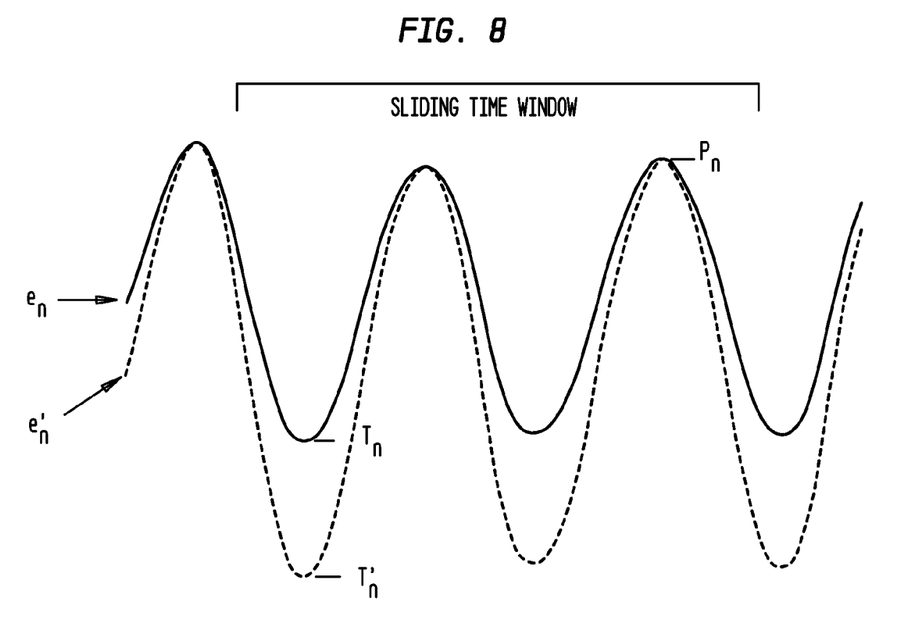
FIGS. 8 and 9 depict example envelope signals for a voiced passage of speech in a single channel and the subsequent modified envelop signals as processed by the MDE algorithm described in Appendix A.1 and A.2 respectively.

Solutions for $C_n$ and $D_n$ 415 (and thus $MD'_n$ 413 and $T'n$ 414) are computed when either the peak or trough levels change. Solution of $e'_n$ 42 is conducted for every time point in the envelope signal. FIG. 8 displays an example unmodified $e_n$ and modified $e'_n$ envelope signal in one channel for a typical voiced passage of speech.

It will be appreciated that the parameters used represent only one possible strategy possible under the implementation described. For example, the inventors have trailed alternative parameters for the strategy. One form uses a knee point of 10 dB, a limit point of 80 dB, and an expansion power of 7 (below the knee point). This provides a greater expansion of modulation depth. Another alternative provides more moderate expansion, with a knee point of 6 dB, a limit of 40 dB, and an expansion power of 4.

The modified envelope signals $e'_n$ replaces the original envelope signals $e_n$ derived from the filter bank and processing then continues as per the original speech coding strategy.

For the SMSP strategy (or the SPEAK and ACE strategies) M of the N channels of $e'_n$ having the largest amplitude at a given instance in time are selected 5 (typically M=8 for this embodiment). The M selected channels are then used to generate M electrical stimuli 6 corresponding in stimulus intensity and electrode number to the amplitude and frequency of the M selected channels. These M stimuli are transmitted to the Cochlear implant 8 via a radio-frequency link 7 and are used to activate M corresponding electrode sites. The modulation depth enhancement may be applied to the channelised sound signal, and subsequent processing continue as per any selected processing strategy for the cochlear implant. This strategy is specific to this stage of processing, and hence is applicable to any strategy which employs channelization and subsequent processing (with modifications as may be dictated by the requirements of the selected strategy).

Figure 4:
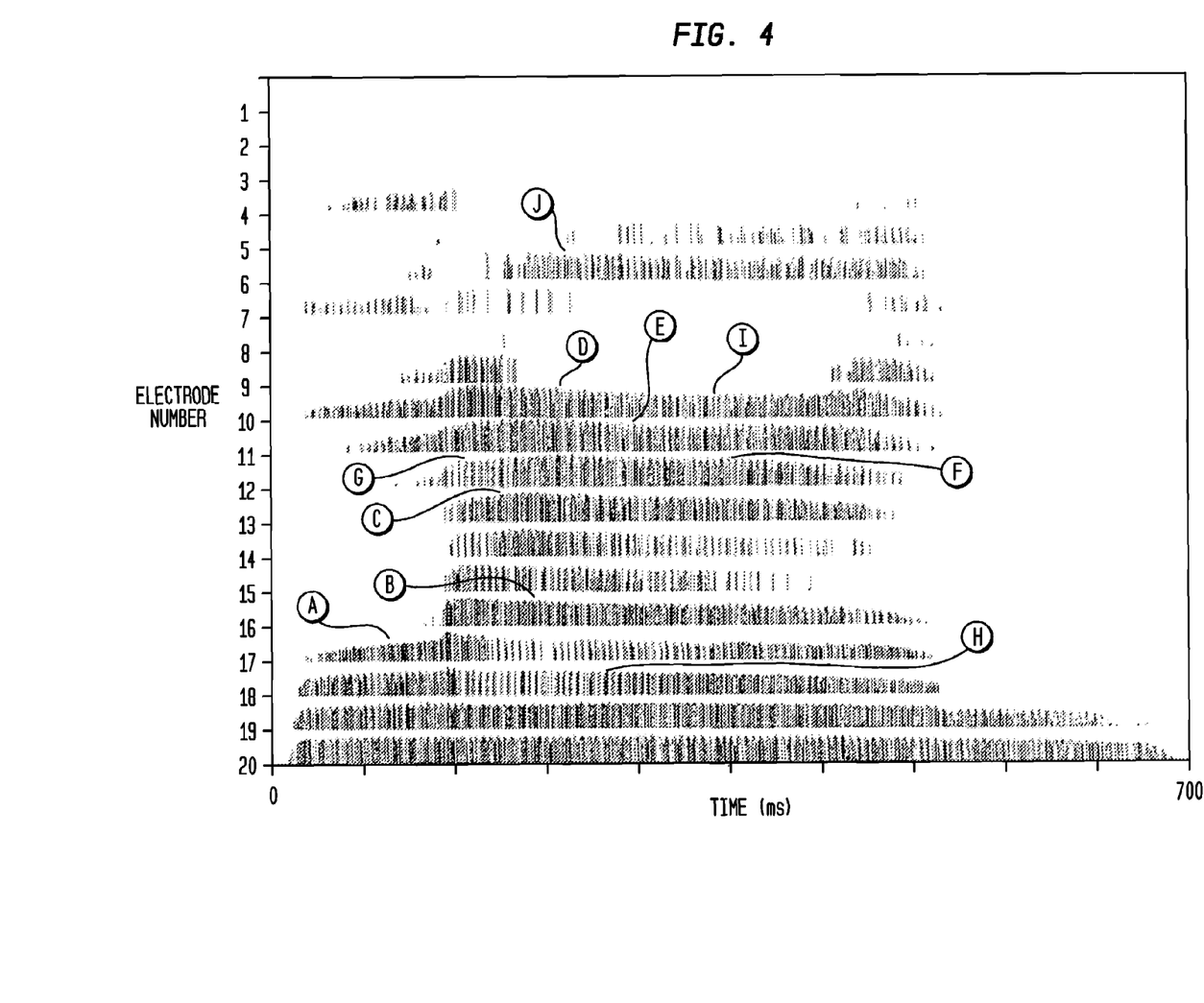
FIGS. 4 and 5 are comparative electrodograms of sound signals to show the effect of the implementation.
Figure 5:
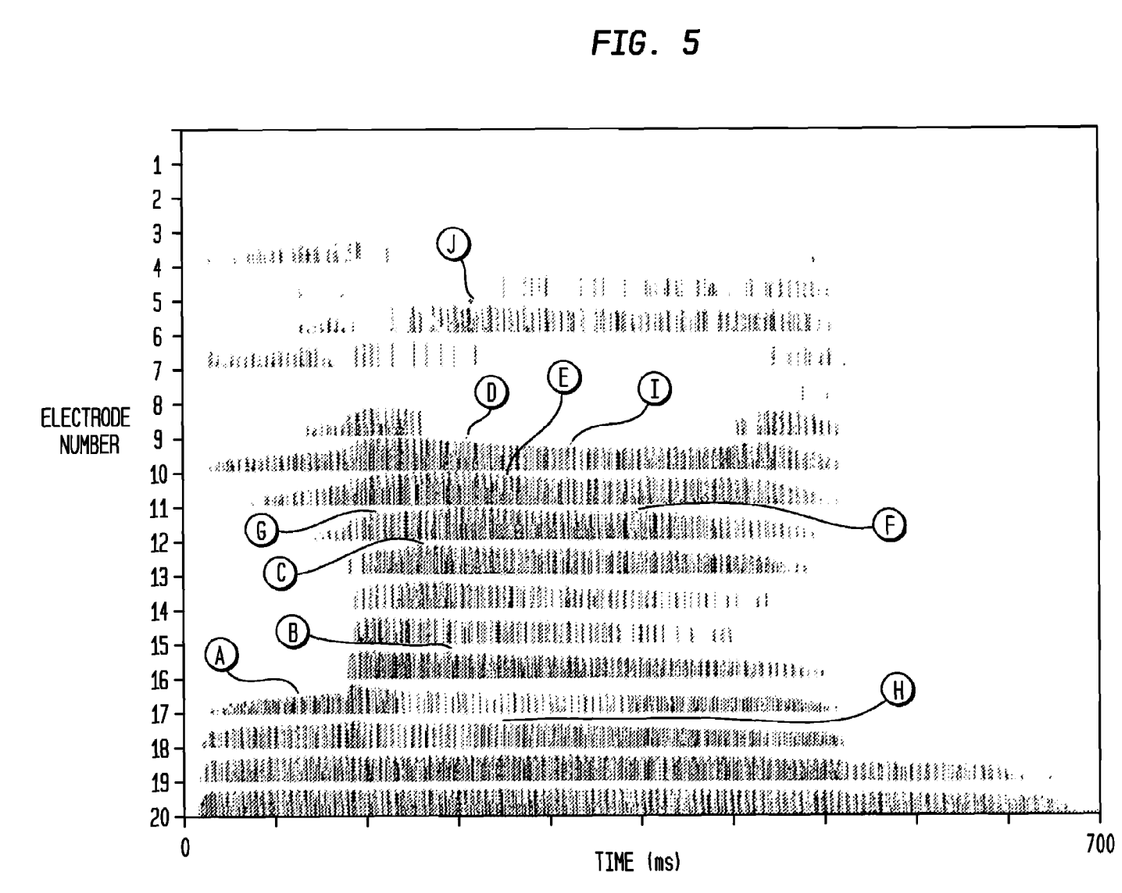

To illustrate the effect of the strategy on the coding of speech signals, stimulus output patterns, known as electrodograms (which are similar to spectrograms for acoustic signals), which plot stimulus intensity (plotted as log current level) for each electrode (channel) as a function of time, were recorded for the SMSP and MDE strategies and are shown in FIGS. 4 & 5 respectively. The speech token presented in these recordings was "lime" and was spoken by a female speaker having a fundamental voicing frequency of approximately 200 Hz. Note, the electrodogram for the MDE strategy depicts the response for the algorithm as described in Appendix A—Approach 2.B. The MDE Knee point was set to 6 dB, the Limit point to 20 dB and the Expansion factor to 3. The effect of the MDE strategy can be seen by comparing FIGS. 4 and 5. For cases where the unmodified modulation depth is small or less than the Knee point (e.g. points A, B and C), the modified modulation depth is expanded by a factor of approximately 3 on a log scale. For cases where the unmodified modulation depth is above the knee point but below the Limit point (e.g. points D, E and F) the modulation depth is still expanded but by a factor less than 3 which approaches 1 as the modulation depth approaches the Limit point. For cases where the unmodified modulation depth is above the Limit point (e.g. points G, H and I), the modulation depth is unmodified. Note, for unvoiced or noisy segments of the signal (e.g. point J) the modulation depth is still modified.

In trials, the inventors have observed the best results in temporal pitch perception have been obtained when the technique described above is combined with a strategy to align temporal peaks across channels. A detailed description of this strategy is annexed as appendix C. In brief, this strategy is applied after the modulation depth has been expanded according to the present invention. The envelope for each channel is determined and temporal peaks identified. A timing offset is then selectively applied to each channel signal, so that the phase differences between the temporal peaks are reduced. These phase adjusted signals are then used as the basis for further processing.

Appendix B provides details on how the MDE algorithm might be implemented in a real-time DSP processing system.

The reader will appreciate that the present invention is of broad application, and that additions or modifications are readily possible within the broad inventive concept disclosed.

Appendix A: Description and Derivation of the MDE Algorithm

Referring to FIGS. 1 and 2 for each channel the modulation depth ($MD_n$), where n refers to channel number, or by definition peak-to-trough ratio of the envelope signal in each channel ($e_n$) can be estimated 412 by dividing the maximum (peak $P_n$) by the minimum (trough $T_n$) levels in $e_n$ as determined 411 over some finite duration using a sliding time window (refer to Eq. A1.1). The duration of the sliding time window ($\tau$) is typically 10 to 15 ms and is sufficiently long enough to analyse fundamental voicing frequencies as low as 100 Hz.

$$MD_n = P_n / T_{ntm} \quad (A1.1)$$

where $P_n$=Maximum level of $e_n$ over sliding time window of duration $\tau$ and $T_n$=Minumum level of $e_n$ over sliding time window of duration $\tau$ Note, for periodic voiced signals such as vowels, the maximum and minimum levels will respectively follow peak and trough envelope signal levels relatively accurately provided that: the voicing period is shorter than the duration ($\tau$) of the sliding time window; and that modulations in the signal at higher harmonics frequencies than the fundamental do not interfere with the modulation depth of the fundamental. For un-voiced signals, such as friction, which have no specific periodicity, the peak and trough levels (and thus the estimated modulation depth) can vary greatly from one peak-trough cycle to the next.

Because the modulation depth is estimated over some finite duration, rather than instantaneously, the estimate must be referenced from a time point corresponding to the middle of the time window. Thus a processing delay of $\tau/2$ is introduced for all processing following the modulation depth estimation. This time shift is to be assumed for the remainder of this description.

The estimated modulation depth ($MD_n$) in each channel could be modified ($MD_n'$) according to some rules that effectively increase the modulation depth in cases when the modulation depth is small.

Approach 1

One possible set of rules 413 that could be used to implement this are described as follows:

(a) For modulation depths less than or equal to some Knee point ($K_{MD}$), the modified modulation depth is increased using a power function where the Expansion Factor ($X_{MD}$), which is typically equal to 2 or 3, defines the order of the power function.

$$MD'_n = MD_n^{X_{MD}} \text{ for } MD_n \leq K_{MD} \quad (A1.2)$$

(b) For modulation depths greater than the Knee point but less than some Limit point ($L_{MD}$), the modulation depth is still increased but a linear function (refer to Eq. A1.3) is used to adjust the modulation depth. The constants A and B can be derived for the following boundary conditions: $MD'_n$ equals $MD_n^{X_{MD}}$ at the knee point (i.e. when $MD_n = K_{MD}$) and $MD_n$ is unchanged (i.e. $MD'_n = MD_n$) at the Limit point. Note, $K_{MD}$ raised to the power of $X_{MD}$ must be less than $L_{MD}$.

$$MD'_n = MD_n \times A + B \quad (A1.3)$$

for $K_{MD} < MD_n < L_{MD}$ and $K_{MD}^{X_{MD}} < L_{MD}$ where $A = (L_{MD} - K_{MD}^{X_{MD}}) / (L_{MD} - K_{MD})$ and $B = L_{MD} \times (1 - A)$ (c) For modulation depths above the Limit point the modulation depth is unchanged.

$$MD'_n = MD_n \text{ for } MD_n \geq L_{MD} \quad (A1.4)$$

FIG. 3 depicts an input/output curve, plotted on a log-log dB scale, for the modulation depth using a Knee point of 2 (6 dB) a Limit point of 10 (20 dB) and an Expansion factor of 3.

The envelope signals ($e_n$) are modified ($e'_n$) so as to achieve the desired modifications to the modulation depth. Recall that the modulation depth is equal to the peak-to-trough ratio of $e_n$ calculated over some finite interval ($\tau$). Thus to increase the modulation depth either the peak level could be increased, the trough level could be decreased, or some function of both increasing the peak and decreasing the trough could be carried out. In order to minimise loudness changes when modifying the modulation depth, it might be desirable to keep the average level of the envelope signal constant. Thus both the peak and trough levels could be adjusted so as to preserve the average level. This approach would be recommended for non-cochlear implant prosthesis (such as hearing aids). However for cochlear implant prostheses, peaks of electrical stimulation contribute mostly to the perceived loudness of the signal and thus to minimise loudness changes, the peaks should be preserved and only the troughs of the envelope signals should be modified.

For cases when the envelope signal is at a trough (i.e. when $e_n = T_n$) the relation shown in Eq. (A1.5) can be used to determine the modified trough level ($T'_n$) which is inversely proportional to the ratio of the modified modulation depth over the original modulation depth 414.

$$T'_n = T_n \times MD_n / MD'_n = P_n / MD'_n \quad (A1.5)$$

However for points in time where the envelope signal is not at a trough, the modified values for the envelope signal (e'n) need to be calculated based on the required reduction to the trough level.

Approach 1A

A simple linear equation could be used to modify the continuum of levels in the envelope signal. The use of a linear function will preserve the shape of the envelope signal within each voicing period (cycle). This linear equation could be of the form shown in Eq. (A1.6). Constants $C_n$ and $D_n$ could be derived 415 such that: the envelope signal is unchanged (i.e. $e'_n = e_n$) when the envelope signal is at a peak; and the envelope signal is adjusted according to the desired modulation depth increase (i.e. $e'_n = e_n \times MD_n / MD'_n$) when the envelope signal is at a trough.

$$e'_n = e_n \times C_n + D_n \quad (A1.6)$$

where $C_n = (P_n - T'_n) / (P_n - T_n)$ and $D_n = P_n \times (1 - C_n)$

Solutions for $C_n$ and $D_n$ 415 (and thus $MD'_n$ 413) would only need to be sought when either the peak or trough levels change. Solution to $e'_n$ 42 would be carried out for every time point in the envelope signal.

Alternate functions rather than a linear equation for modification of the continuum of levels in the envelope signal could be employed. For instance, it may be desirable to better preserve the peak level by using a $2^{nd}$ or higher order equation that adjusts levels in the through region (i.e. levels below the average or mid-point of the envelope signal) more than those in the peak region (i.e. levels above the mid-point of the envelope signal). This would ensure less change to the loudness of the peaks and thus less change to the overall loudness of the perceived signal after processing. It will however distort the shape of the envelope signal within each voicing period.

Approach 1B

Rather than using a $2^{nd}$ or higher order equation an alternate approach might use a linear equation but change the boundary conditions such that only trough regions (i.e. levels below the mid-point of the envelope signal) are modified. The mid-point of the envelope signal could be defined as follows:

$$M_n=(P_n+T_n)/2 \tag{A1.7}$$

For cases when the envelope signal is above the mid-point no change to the signal would be applied. However for cases when the envelope signal is below the mid-point a linear equation could be employed to modify the signal such that mid-point levels are unchanged but levels at a trough are decreased by the desired increase to the modulation depth. The same linear equation as used above (i.e. Eq. A1.6) could be used but the constants $C_n$ and $D_n$ would be adjusted by making reference to the mid-point $M_n$.

$$e'_n=e_n \times C_n+D_n \text{ for } e_n<M_n \tag{A1.8}$$

where $C_n=(M_n-T'_n)/(M_n-T_n)$ and $D_n=M_n \times (1-C_n)$

Figure 9:
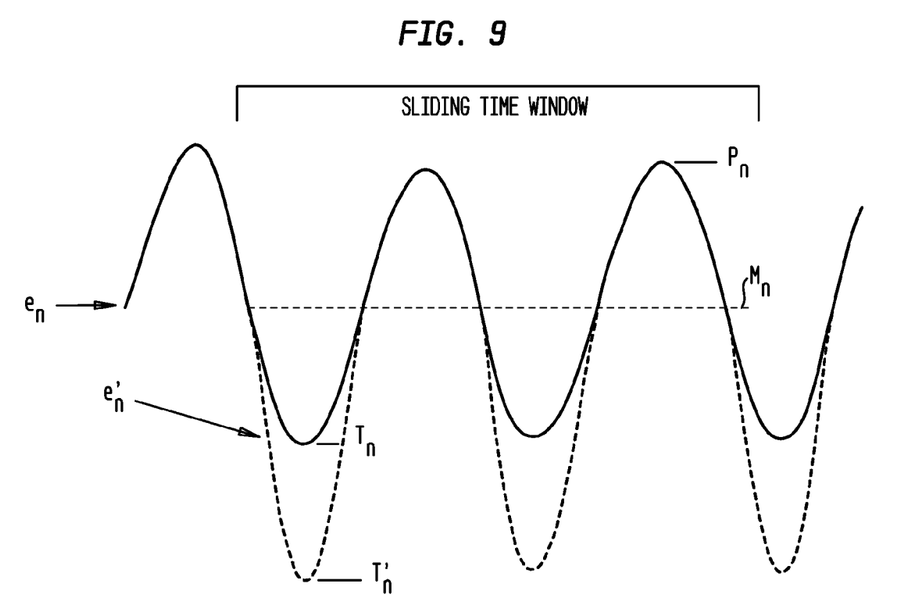

Note, the above approach will preserve the shape of the signal when it is above the mid-point and then stretch the signal when it is below the mid-point. FIG. 9 displays an example unmodified ($e_n$) and modified ($e'_n$) envelope signal for this approach. Note also that the schematic shown in FIG. 2 for Approach 1.A also applies for Approach 1.B, however an extra calculation for the mid-point level ($M_n$) is required in 411 and calculation of $C_n$ and $D_n$ in 415 will be relative to the mid-point rather than the peak level.

Approach 2

Approach 2A

Figure 6:
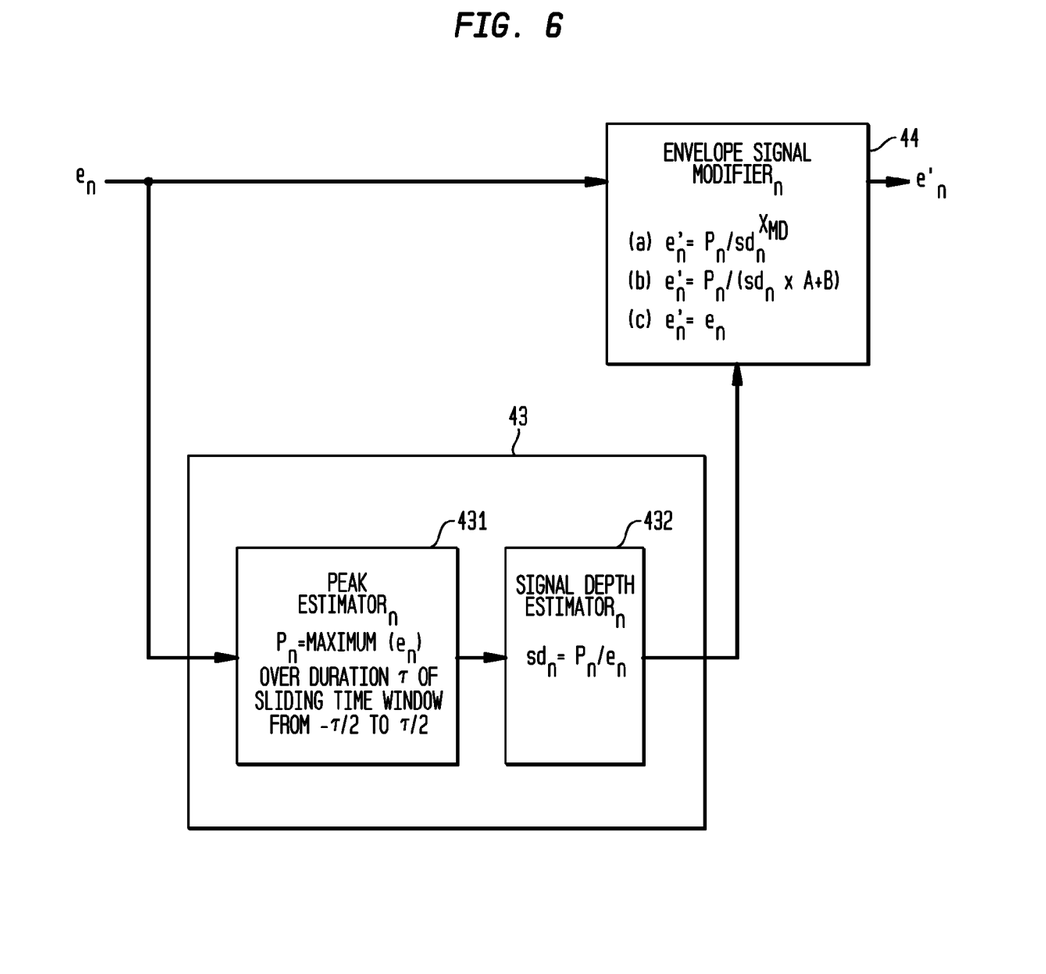
FIGS. 6 and 7 are schematic representations of the signal processing applied by the MDE algorithm described in Appendix A—Approaches 2.A and 2.B respectively.

An alternative approach for implementation of the algorithm could adjust the envelope signal based on the "signal depth" rather than the total modulation depth. Referring to FIG. 6, which replaces the processing shown in FIG. 2, the "signal depth" ($sd_n$) 432 could represents the ratio of the peak level 431 to the envelope signal level at any time point and be defined as shown in Eq. (A2.1). The "signal depth" will equal the true modulation depth when the signal is at a trough and will equal unity when the signal is at a peak. For all levels between the peak and trough the "signal depth" will be inversely proportional to the signal level.

$$sd_n=P_n/e_n \tag{A2.1}$$

The "signal depth" is calculated continuously and used to adjust the envelope signal level for all time points. Applying similar rules to those used in Approach 1 for modification of the modulation depth, and using the relation $e'_n=P_n/sd'_n$ we can establish equations for the modified envelope signal levels as a function of the "signal depth" 44.

(a) For "signal depths" less than or equal to the Knee point:

$$e'_n=P_n/sd_n^{XMD} \tag{A2.2}$$

for $sd_n \leq K_{MD}$ (b) For "signal depths" greater than the Knee point but less than the Limit point:

$$e'_n=P_n/(sd_n \times A+B) \tag{A2.3}$$

for $K_{MD}<sd_n<L_{MD}$ and $K_{MD}^{XMD}<L_{MD}$ where $A=(L_{MD}-K_{MD}^{XMD})/(L_{MD}-K_{MD})$ and $B=L_{MD} \times (1-A)$ (c) For "signal depths: above the Limit point the envelope signal level is preserved.

$$e'_n=e_n \text{ for } sd_n \geq L_{MD} \tag{A2.4}$$

Approach 2.B

As in Approach 1.B the loudness of the processed signal might be better preserved by restricting signal modification to time points in which the envelope signal is less than the mid-point (Mn as defined in Eq. A1.7) between its peak and trough levels. In addition, computational time would be reduced as calculation of the "signal depth" is expensive as it requires a divide operation.

Modification of the envelope signal could simply be restricted to points in which the envelope signal is less than the mid-point (i.e. $e_n<M_n$). As pointed out in Approach 1.B this will introduce distortion of the envelope signal (i.e. a step change in the envelop signal level) at values around the mid-point. However, for cochlear implant prostheses this may not pose a big problem as it is unlikely that this sort of distortion is noticeable or destructive to the signal. For non-cochlear implant prostheses (such as hearing aids) this sort of distortion may be noticeable and should be avoided. In fact even Approach 2.A can introduce inter-period distortion that may be noticeable and thus Approach 1 is recommended for non-cochlear implant prostheses.

The distortion discussed above may be alleviated somewhat by re-defining the equation for the "signal depth", as shown in Eq. (A2.1), as a function of the mid-point, rather than the peak, of the envelope signal level.

$$sd_n=M_n/e_n \text{ for } e_n<M_n \tag{A2.5}$$

However the "signal depth" $sd_n$ now no longer equals the modulation depth when the signal is at a trough. Modifying Eq. (A2.5) so that the boundary conditions of: $sd_n=1$ at the mid-point (i.e. for $e_n=M_n$); and $sd_n=MD_n$ at a trough (i.e. for $e_n=T_n$) are met we obtain:

$$sd_n=(2 \times M_n-e_n)/e_n \text{ for } e_n<M_n \tag{A2.6}$$

Figure 7:
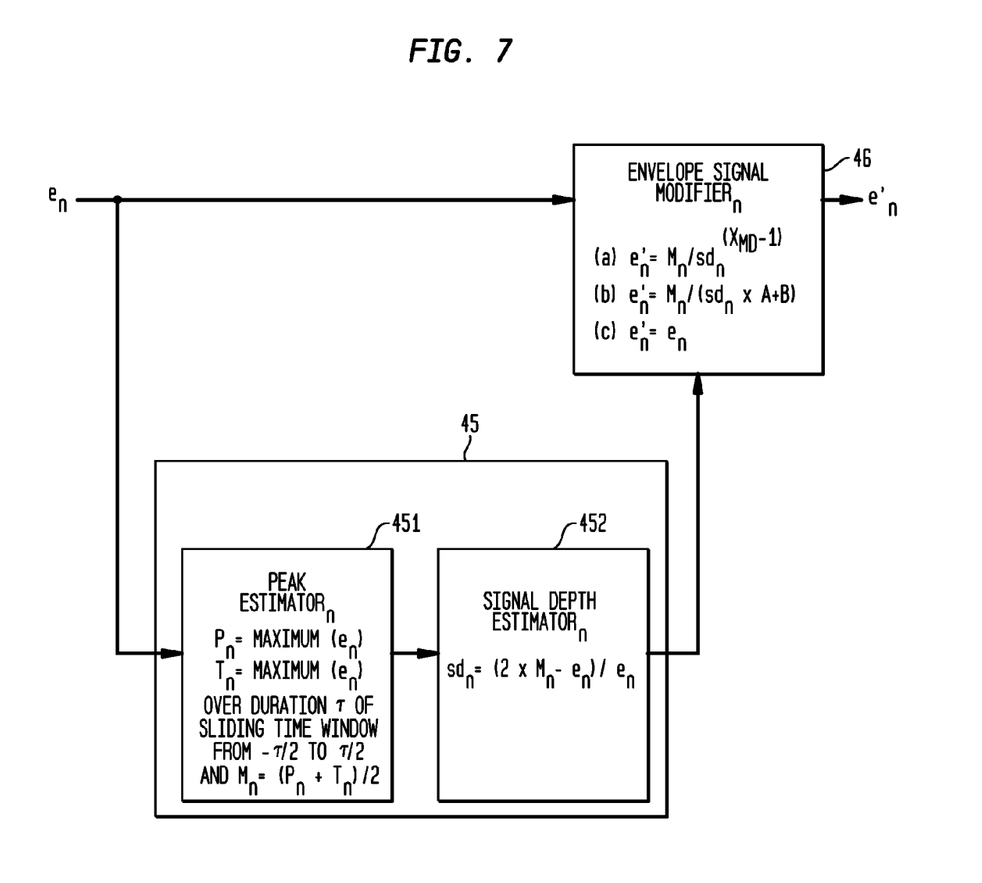

Referring to FIG. 7, which replaces the processing shown in FIG. 6, similar modulation depth rules as used above in Eqs. (A2.2) to (A2.4) can be used to derive equations for the modified envelope signal (e'n) 46 as a function of the "signal depth" 452 as defined in Eq. (A2.6) for all time point in en which are less than the mid-point Mn 451.

(a) For "signal depths" less than or equal to the Knee point:

$$e'_n=M_n/sd_n^{(XMD-1)} \tag{A2.7}$$

for $sd_n \leq K_{MD}$ and $e_n<M_n$ (b) For "signal depths" greater than the Knee Point but less than the Limit point:

$$e'_n=M_n/(sd_n \times A+B) \tag{A2.8}$$

for $K_{MD}<sd_n<L_{MD}$ and $K_{MD}^{XMD}<L_{MD}$ and $e_n<M_n$ where $A=(L_{MD}-K_{MD}^{XMD})/(2 \times (L_{MD}-K_{MD}))$ and $B=L_{MD} \times A+(1-L_{MD})/2$ (c) For "signal depths: above the Limit point the envelope signal level is preserved.

$$e'_n=e_n \text{ for } sd_n \geq L_{MD} \tag{A2.9}$$

Note however that the rules differ slightly from those in Approach 2.A because the "signal depth" is now relative to the mid-point, rather than the peak. In addition, for cases in which the modulation depth (or "signal depth") is small (i.e. less than the knee point), the modulation depth expansion factor will be less than $X_{MD}$ (i.e. approximately $X_{MD}-0.5$).

Appendix B: Conversion of MDE Algorithm to a Form Suitable for Real-time DSP Processing In converting the MDE algorithm to a form suitable for real-time DSP processing two main criteria need to taken into consideration. Firstly fixed-point DSP processing deals with numerical values less than or equal to 1.0. Thus when dealing with parameters in the algorithm such the modulation depth (i.e. the ratio of the peak-to-trough level which is a value that is always greater than or equal 1.0) the parameters must either be scaled such that they fall into a usable range below 1.0, or inverted (i.e. reciprocal) such that they will never be greater than 1.0. For the case of the modulation depth (and "signal depth") it was chosen to deal with inverted values. Secondly, DSP processors are typically efficient at performing add, subtract and multiply operations, but not divisions. Thus the processing should be arranged so as to minimise the number of division operations required.

Approach 1

Conversion of the MDE algorithm described in Appendix A—Approach 1 is described below. The modulation depth as per Eq. (A1.1) is inverted so as to never exceed 1.0.

$$MD_n = e_n/P_n \quad (B1.1)$$

The Knee point and Limit point are subsequently inverted and Eqs. (A1.2) to (A1.4) can be re-written as follows:

(a) For inverted "signal depths" greater than or equal to the inverted Knee point:

$$MD'_n = MD_n^{X_{MD}} \text{ for } MD_n \leq K_{MD} \quad (B1.2)$$

(b) For inverted "signal depths" less than the inverted Knee point but greater than the inverted Limit point:

$$MD'_n = MD_n \times A + B \quad (B1.3)$$

for $K_{MD} < MD_n < L_{MD}$ and $K_{MD}^{X_{MD}} < L_{MD}$ where $A = (L_{MD} - K_{MD}^{X_{MD}})/(L_{MD} - K_{MD})$ and $B = L_{MD} \times (1 - A)$ (c) For inverted "signal depths" less than the inverted Limit point the envelope signal level is preserved.

$$MD'_n = MD_n \text{ for } MD_n \geq L_{MD} \quad (B1.4)$$

The modified trough level (Eq. A1.5) can be expressed as a function of the modified inverted modulation depth ($MD'_n$).

$$T'_n = P_n \times MD'_n \quad (B1.5)$$

Approach 1.A

For Approach 1.A, the modified envelope signal is defined as:

$$e'_n = e_n \times C_n + D_n \quad (B1.6)$$

where $C_n = (P_n - T'_n)/(P_n - T_n)$ and $D_n = P_n \times (1 - C_n)$

Note however that the constant $C_n$ will always be greater than or equal to 1.0. Inverting $C_n$ will require a divide operation for each calculation of $e'_n$, thus it would be more efficient to scale $C_n$ (and thus $D_n$) by a factor of $1/S$ (where $S = 2^{12}$ for a 24-bit DSP) when storing these constants and inverse scaling of S can be applied to Eq. (B1.6) as shown in Eq. (B1.7). It is efficient to scale by a power of 2 because this can typically be performed using a barrel right or left shift operation in a DSP rather than a divide or multiply operation respectively.

$$e'_n = (e_n \times C'_n + D''_n) \times S \quad (B1.7)$$

where $C'_n = (1/S) \times (P_n - T'_n)/(P_n - T_n)$ and $D'_n = P_n \times (1/S - C'_n)$ Approach 1.B For Approach 1.B, the constants C'n and D'n used in Eq. (B1.7) can be defined as follows.

$$C'_n = (1/S) \times (M_n - T'_n)/(M_n - T_n) \text{ and } D'_n = M_n \times (1/S - C'_n)$$

Approach 2

Approach 2.A

Conversion of the MDE algorithm described in Appendix A—Approach 2.A is described below. The "signal depth" as per Eq. (A2.1) is inverted so as to never exceed 1.0.

$$sd_n = e_n/P_n \quad (B2.1)$$

The Knee point and Limit point are subsequently inverted and Eqs. (A2.2) to (A2.4) can be re-written as follows:

(a) For inverted "signal depths" greater than or equal to the inverted Knee point:

$$e'_n = P_n \times sd_n^{X_{MD}} \text{ for } sd_n \geq K_{MD} \quad (B2.2)$$

(b) For inverted "signal depths" less than the inverted Knee point but greater than the inverted Limit point:

$$e'_n = P_n \times (sd_n \times A + B) \quad (B2.3)$$

for $K_{MD} > sd_n > L_{MD}$ and $K_{MD}^{X_{MD}} > L_{MD}$ where $A = (L_{MD} - K_{MD}^{X_{MD}})/(L_{MD} - K_{MD})$ and $B = L_{MD} \times (1 - A)$ (c) For inverted "signal depths" less than the inverted Limit point the envelope signal level is preserved.

$$e'_n = e_n \text{ for } sd_n \leq L_{MD} \quad (B2.4)$$

Approach 2.B

Equations (B2.2) to (B2.4) can be employed with the restriction that the "signal depth" and thus the modified envelope signal level is only calculated when the envelope signal level is less than the mid-point level.

Alternatively, distortion may be alleviated by re-defining the "signal depth" as per Eq. (A2.6). Again the "signal depth" must be inverted so as to never exceed 1.0.

$$sd_n = e_n/(2 \times M_n - e_n) \text{ for } e_n < M_n \quad (B2.5)$$

The Knee point and Limit point are subsequently inverted and Eqs. (A2.7) to (A2.9) can be re-written as follows:

(a) For inverted "signal depths" greater than or equal to the inverted Knee point:

$$e'_n = M_n \times sd_n^{(X_{MD} - 1)} \text{ for } sd_n \geq K_{MD} \text{ \& } e_n < M_n \quad (B2.6)$$

(b) For inverted "signal depths" less than the inverted Knee point but greater than the inverted Limit point:

$$e'_n = M_n \times (sd_n \times A + B) \quad (B2.7)$$

for $K_{MD} > sd_n > L_{MD}$ & $K_{MD}^{X_{MD}} > L_{MD}$ & $e_n < M_n$ where $A = \dfrac{2 \times (L_{MD} - K_{MD}^{X_{MD}})}{(L_{MD} - K_{MD}) \times (1 + L_{MD}) \times (1 + K_{MD}^{X_{MD}})}$ and $B = L_{MD} \times (2/(1 + L_{MD}) - A)$ (c) For inverted "signal depths" less than the inverted Limit point the envelope signal level is preserved.

$$e'_n = e_n \text{ for } sd_n \leq L_{MD} \quad (B2.8)$$

REFERENCES

Abberton, E., & Fourcin, A. (1978). "Intonation and speaker identification," Lang. Speech 21, 305-318.

Brokx, J. P. L., & Nooteboom, S. G. (1982). "Intonation and the perceptual separation of simultaneous voices," J. Phonetics, 10, 23-36.

Ciocca, V., Francis, A. L., Aisha, R., & Wong, L. (2002). "The perception of Contonese lexical tones by early-deafened cochlear implantees," J. Acoust. Soc. Am. 111, 2250-2256.

Highnam, C., & Morris, V. (1987). "Linguistic stress judgments of language learning disabled students," J. Commun. Disord. 20, 93-103.

Liberman, P., & Michaels, S. B. (1962). "Some aspects of fundamental frequency and envelope amplitude as related to the emotional content of speech," J. Acoust. Soc. Am. 34, 922-927.

Lee, K. Y. S., van Hasselt, C. A., Chiu, S. N., & Cheung, D. M. C. (2002). "Cantonese tone perception ability of cochlear implant children in comparison with normal-hearing children," Int. J. Ped. Otolaryngol. 63, 137-147.

McDermott, H. J., & Vandali, A. E. (1991). "Spectral Maxima Sound Processor," Australian Patent, 657959; U.S. Pat. No. 788591.

McDermott, H. J., McKay, C. M., & Vandali, A. E. (1992). "A new portable sound processor for the University of Melbourne/Nucleus Limited multielectrode cochlear implant," J. Acoust. Soc. Am. 91, 3367-3371.

McKay, C. M., McDermott, H. J., & Clark, G. M (1994). "Pitch percepts associated with amplitude-modulated current pulse trains by cochlear implantees," J. Acoust. Soc. Am. 96, 2664-2673.

McKay, C. M., & McDermott, H. J. (1995). "The perception of temporal patterns for electrical stimulation presented at one or two intracochlear sites," J. Acoust. Soc. Am. 100, 1081-1092

Moore, B. C. J. (1995). "Hearing" in *The handbook of Perception and Cognition* (2nd ed.), edited by B. C. J. Moore (Academic Press, Inc., London), pp 267-295.

Nooteboom, S. (1997). "The prosody of speech: Melody and rhythm," in *The handbook of Phonetic Sciences*, edited by W.J. Hardcastle and J. Laver (Blackwell, Oxford), pp 640-673.

Seligman, P. M., Dowell, R. C., Blamey, P. J. (1992). "Multi Peak Speech Procession," U.S. Pat. No. 5,095,904.

Skinner, M. W., Holden, L. K., Holden, T. A., Dowell, R. C., Seligman, P. M., Brimacombe, J. A., & Beiter, A. L. (1991). "Performance of postlinguistically deaf adults with the Wearable Speech Processor (WSP III) and the Mini Speech Processor (MSP) of the Nucleus multi-electrode cochlear implant," Ear and Hearing, 12, 3-22.

Skinner, M. W., Clark, G. M., Whitford, L. A., Seligman, P. A., Staller, S. J., Shipp, D. B., Shallop, J. K., Everingham, C., Menapace, C. M., Arndt, P. L., Antogenelli, T., Brimacombe, J. A., & Beiter, A. L. (1994). "Evaluation of a new spectral peak (SPEAK) coding strategy for the Nucleus 22 channel cochlear implant system," The Am. J. Otology, 15, (Suppl. 2), 15-27.

Vandali, A. E., Whitford, L. A., Plant, K. L., & Clark, G. M. (2000). "Speech perception as a function of electrical stimulation rate: Using the Nucleus 24 Cochlear implant system," Ear & Hearing, 21, 608-624.

Wells, B., Peppe, S., & Vance, M. (1995). "Linguistic assessment of prosody," in *Linguistics in Clinical Practice*, edited by K. Grundy (Whurr, London), pp 234-265.

Whitford, L. A., Seligman, P. M., Everingham, C. E., Antognelli, T., Skok, M. C., Hollow, R. D., Plant, K. L., Germ, E. S., Staller, S. J., McDermott, H. J., Gibson, W. R., Clark, G. M. (1995). "Evaluation of the Nucleus Spectra 22 processor and new speech processing strategy (SPEAK) in post-linguistically deafened adults," Acta Oto-laryngologica (Stockholm), 115, 629-637.

Wilson, B. S., Finley, C. C., Lawson, D. T., Wolford, R. D., Eddington, D. K., & Rabinowitz, W. M. (1991). "Better speech recognition with cochlear implants," Nature, 352, 236-238.

What is claimed is:

1. A sound processing process including at least the steps of: (a) receiving a sound signal; (b) processing said sound signal so as to produce a set of signals in spaced frequency channels; and (c) performing further processing upon at least some of the set of signals; wherein said process further includes the step of selectively increasing the modulation depth of the envelope signal for at least selected channels in response to a predetermined instruction set, prior to step (c).

2. A sound processing process according to claim 1, wherein the modulation depth is estimated for a channel after step (b) by calculating the ratio of the peak amplitude to the trough amplitude of the envelope signal over a time duration sufficient to allow for fundamental voicing frequencies to be determined.

3. A sound processing process according to claim 1, wherein the modulation depth is adjusted by reducing the trough amplitude while substantially preserving the value of the peak amplitudes.

4. A sound processing process according to claim 2, wherein the level of increase of modulation depth for a channel is dependant upon the value of the modulation depth.

5. A sound processing process according to claim 4, wherein if the modulation depth is below a predetermined value K, the modulation depth is increased by a power function;

if the modulation depth is greater that K and smaller than a limit point L, then the modulation depth is increased by a linear function; and if the modulation depth is greater than L, the modulation depth is not modified.

6. A sound processing process according to claim 1, wherein the modulation depth is adjusted by increasing the value of the peak amplitudes and reducing the value of the trough amplitudes.

7. A sound processing process according to claim 1, wherein the shape of the modulation peaks within the channel are substantially preserved after the change to the modulation depth.

8. A sound processing process according to claim 1, wherein the process is carried out for an auditory prosthesis.

9. A sound processing process according to claim 8, wherein the process is carried out prior to applying a speech processing strategy.

10. A sound processing process according to claim 9, wherein the auditory prosthesis is a cochlear implant.

11. An auditory prosthesis or part thereof, including software intended to operatively carry out the process of claim 8.

* * * * *